United States Patent
Ishige et al.

(10) Patent No.: US 6,218,598 B1
(45) Date of Patent: Apr. 17, 2001

(54) PLANT PROMOTER

(75) Inventors: Fumiharu Ishige, Kobe; Satomi Nishikawa, Ashiya; Kenji Oeda, Kyoto, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/352,608

(22) Filed: Jul. 13, 1999

(30) Foreign Application Priority Data

Jul. 15, 1998 (JP) .................................................. 10-200372

(51) Int. Cl.⁷ .............................. C12N 5/04; C12N 15/11; C12N 15/29; C12N 15/82; A01H 5/00
(52) U.S. Cl. ......................... 800/278; 800/287; 800/298; 435/69.1; 435/419; 435/468; 435/252.3; 435/320.1; 536/24.1; 536/25.3; 536/23.1; 536/23.6
(58) Field of Search .................... 536/24.1, 23.1, 536/25.3, 23.6; 435/320.1, 419, 468, 252.3, 69.1; 800/287, 298, 278

(56) References Cited

U.S. PATENT DOCUMENTS 5,959,176 * 9/1999 Torikai et al. ........................ 800/287

FOREIGN PATENT DOCUMENTS

| 571741 A2 | * 12/1993 | (EP) . |
|---|---|---|
| 0571741A2 | 12/1993 | (EP) . |
| 0754757A2 | 1/1996 | (EP) . |
| 754757A2 | 1/1997 | (EP) . |
| 0824150A2 | 2/1998 | (EP) . |

OTHER PUBLICATIONS

Drew , R. L. K. Hort. Res. vol. 19, pp. 79–84, 1979.*
Ishige, Fumiharu et al., The Plant Journal, vol. 18, No. 4 (1999), pp. 443–448.

* cited by examiner

Primary Examiner—David T. Fox
Assistant Examiner—Medina A. Ibrahim
(74) Attorney, Agent, or Firm—Birch, Stewart, Kolasch & Birch, LLP

(57) ABSTRACT

The present invention provides a promoter which is characterized in that it has following DNA sequence (a) or (b) and a DNA having the nucleotide sequence shown by SEQ ID:No.1, (a) a DNA sequence having the nucleotide sequence represented by at least nucleotide numbers 112–246 within the nucleotide sequence shown by SEQ ID:No.2, (b) a DNA sequence having the nucleotide sequence represented by at least base numbers 186–282 within the nucleotide sequence shown by SEQ ID:No.3 (hereinafter referred to as the present promoter), a chimera gene having the above promoter, a vector having the above promoter, a transformant characterized in that the promoter, the chimera gene or the vector is introduced into a host cell, a method for expressing gene comprising a step of expressing the desired gene in a host cell under the control of the promoter, use of the promoter for controlling the expression of a desired gene in a host cell, and a method for producing the promoter. According to the present invention, there becomes possible to provide a compact promoter suitable for more highly expressing the desired gene in the particular tissue than in other tissues in a host.

21 Claims, 5 Drawing Sheets

SEQUENCE LISTING

<160> NUMBER OF SEQ ID NOS: 20

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:primer

<400> SEQUENCE: 1
gccacgtgcc                                                                  10

<210> SEQ ID NO 2
<211> LENGTH: 246
<212> TYPE: DNA
<213> ORGANISM: Daucus carota

<400> SEQUENCE: 2
tctagaatat atcttttgaa atttcaacaa acacagcact aactttttctt ttaacagatt        60 agaatcgttt cctaaacttt taaaattaaa aaatacatta ctataatatt tatcaacacc       120
tcaacattca tgttagcgta ctataaatag gtgctcttgg tgctctacta tcatcacatc       180
aatcttccag cacaaacctt gagcttaatc tttctactaa tttttagcaa aaacattcta       240
aaggtc                                                                    246

```
<210> SEQ ID NO 3
<211> LENGTH: 282
<212> TYPE: DNA
<213> ORGANISM: Glycine max

<400> SEQUENCE: 3
gaaaccatgc atggtccct cgtcatcacg agtttctgcc atttgcaata gaaacactga    60
aacacctttc tctttgtcac ttaattgaga tgccgaagcc acctcacacc atgaacttca   120
tgaggtgtag cacccaaggc ttccatagcc atgcatactg aagaatgtct caagctcagc   180
accctacttc tgtgacgtgt ccctcattca ccttcctctc ttccctataa ataaccacgc   240
ctcaggttct ccgcttcaca actcaaacat tctctccatt gg                     282

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 4
agcttgccac gtgccgccac gtgccgccac gtgccgccac gtgcct                  46

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence:primer

<400> SEQUENCE: 5
ctagaggcac gtggcggcac gtggcggcac gtggcggcac gtggca                  46

<210> SEQ ID NO 6
<211> LENGTH: 140
<212> TYPE: DNA
<213> ORGANISM: Artificial Sequence
<220> FEATURE:
<223> OTHER INFORMATION: Description of Artificial Sequence:primer

<400> SEQUENCE: 6
ctagatcaac acctcaacat tcatgttagc gtactataaa taggtgctct tggtgctcta    60
ctatcatcac atcaatcttc cagcacaaac cttgagctta atctttctac taattttag   120 caaaaacatt ctaaaggtcg                                               140

<210> SEQ ID NO 7
<211> LENGTH: 140
<212> TYPE: DNA
<213> ORGANISM: Artificial Sequence
<220> FEATURE:
<223> OTHER INFORMATION: Description of Artificial Sequence:primer

<400> SEQUENCE: 7
gatccgacct ttagaatgtt tttgctaaaa attagtagaa agattaagct caaggtttgt    60
gctggaagat tgatgtgatg atagtagagc accaagagca cctatttata gtacgctaac   120
atgaatgttg aggtgttgat                                               140

<210> SEQ ID NO 8
<211> LENGTH: 28
<212> TYPE: DNA
```

```
<213> ORGANISM: Artificial Sequence
<220> FEATURE:
<223> OTHER INFORMATION: Description of Artificial Sequence:primer

<400> SEQUENCE: 8
aaggatccga cctttagaat gttttttgc                                          28

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 9
tctctagatc aacacctcaa cattc                                              25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 10
tctctagaca gattagaatc gtttcc                                             26

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 11
gccagtgaat gctttctag                                                     19

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 12
aaggatccaa tggagagaat gt                                                 22

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 13
tctctagact tctgtgacgt gtccc                                              25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 14
tctctagagt agcacccaag gcttc                                              25
```

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 15
tctctagaga aaccatgcat ggtcc                                    25

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 16
catgcttaac gtaattcaac ag                                       22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 17
acatgtggag tgaagagtat c                                        21

<210> SEQ ID NO 18
<211> LENGTH: 118
<212> TYPE: DNA
<213> ORGANISM: Artificial Sequence
<220> FEATURE:
<223> OTHER INFORMATION: Description of Artificial Sequence:primer

<400> SEQUENCE: 18
gattacgcca agcttgccac gtgccgccac gtgccgccac gtgccgccac gtgccgccac     60
gtgccgccac gtgccgccac gtgccgccac gtgcctctag atcaacacct caacattc      118

<210> SEQ ID NO 19
<211> LENGTH: 119
<212> TYPE: DNA
<213> ORGANISM: Artificial Sequence
<220> FEATURE:
<223> OTHER INFORMATION: Description of Artificial Sequence:primer

<400> SEQUENCE: 19
gattacgcca agcttgccac gtgccgccac gtgccgccac gtgccgccac gtgccgccac     60
gtgccgccac gtgccgccac gtgccgccac gtgcctctag acagattaga atcgtttcc    119

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 20
ctgccagttc agttggttgt tcacac                                   26

PLANT PROMOTER

BACKGROUND OF THE INVENTION

1. Field of the Invention

The present invention relates to a promoter functional in a plant cell.

2. Description of the Related Art

In order to express the desired gene in a host cell for altering traits of a host cell such as a plant cell, etc., the gene is placed under the control of a promoter functional in a host cell. When it is necessary to more highly express the desired gene in a specified tissue of a host than other tissues, a promoter conferring the higher transcription activity in the specified tissue than in the other tissues is used.

The promoter which has a longer DNA sequence is influenced by a variety of factors in a host cell or probability of recombination or deletion is increased when the promoter is introduced into a chromosome of a host cell. As a result, there arises a problem that the desired trait is not expressed when the promoter is introduced into a host cell.

Then, there has been a demand for a compact promoter which may be suitable for higher expression of the desired gene in the particular tissue than in the other tissues in a host.

DISCLOSURE OF THE INVENTION

Under these circumstances, the present inventors studied hard and, as a result, found the particular nucleotide sequence suitable for the above object, which resulted in completion of the present invention.

That is, the present invention provides:

1. a promoter which is characterized in that it has following DNA sequence (a) or (b) and a DNA having the nucleotide sequence shown by SEQ ID:No.1,
   (a) a DNA sequence having the nucleotide sequence represented by at least nucleotide numbers 112–246 within the nucleotide sequence shown by SEQ ID:No.2,
   (b) a DNA sequence having the nucleotide sequence represented by at least base numbers 186–282 within the nucleotide sequence shown by SEQ ID:No.3 (hereinafter referred to as the present promoter),
2. a promoter which is characterized in that it has the following DNA sequence (a) or (b) and a DNA having the nucleotide sequence shown by SEQ ID:No.1,
   (a) a DNA sequence represented by nucleotide numbers 112–246, nucleotide numbers 54–246 or nucleotide numbers 1–246 within the nucleotide sequence shown by SEQ ID:No.2,
   (b) a DNA sequence represented by nucleotide numbers 186–282, nucleotide numbers 127–282 or nucleotide numbers 1–282 within the nucleotide sequence shown by SEQ ID:No.3,
3. the promoter according to 1 or 2, wherein a DNA having the nucleotide sequence shown by SEQ ID:No.1 is positioned 5' upstream of the DNA sequence (a) or (b),
4. the promoter according to any one of 1–3, which is characterized in that it has two or more than two copies of the nucleotide sequence shown by SEQ ID:No.1,
5. the promoter according to claims 1 to 3, which is characterized in that it has 4 or 8 copies of the nucleotide sequence shown by SEQ ID:No.1,
6. a chimera gene which is characterized in that it has the promoter of any one of 1–5 and a desired gene (hereinafter referred to as the present chimera gene),
7. a vector which is characterized in that it has the promoter of any one of 1–5 (hereinafter referred to as the present vector),
8. the vector according to 7, which is characterized in that it has a cloninig site and a terminator functional in a host cell, which is positioned 3' downstream of the promoter,
9. a vector which is characterized in that it has the chimera gene of 6,
10. a transformant which is characterized in that the promoter of any one of 1–5, the chimera gene of 6 or the vector of any one of 7–9 is introduced into a host cell (hereinafter referred to as the present transformant),
11. the transformant according to 10, which is characterized in that the host cell is a microorganism,
12. the transformant according to 10, which is characterized in that the host cell is a plant cell,
13. a method for expressing gene, which is characterized by comprising a step of expressing the desired gene in a host cell under the control of the promoter of any one of 1–5 (hereinafter referred to as the present gene expression method),
14. use of the promoter of any one of 1–5 for controlling the expression of a desired gene in a host cell,
15. a method for producing a promoter, which is characterized by comprising a step of ligating a DNA having the following DNA sequence (a) or (b) and a DNA having the nucleotide sequence shown by SEQ ID:No.1 in an functional form in a host cell (hereinafter referred to as the present promoter manufacturing process),
    (a) A DNA sequence having the nucleotide sequence represented by at least nucleotide numbers 112–246 within the nucleotide sequence shown by SEQ ID:No.2,
    (b) A DNA sequence having the nucleotide sequence represented by at least nucleotide numbers 186–282 within the nucleotide sequence shown by SEQ ID:No.3,
16. a method for producing a promoter, which is characterized by comprising a step of ligating a DNA having the following DNA sequence (a) or (b) and a DNA having the nucleotide sequence shown by SEQ ID:No.1 in an functional form in a host cell,
    (a) a DNA sequence represented by nucleotide numbers 112–246, nucleotide numbers 54–246 or nucleotide numbers 1–246 within the nucleotide sequence shown by SEQ ID:No.2,
    (b) a DNA sequence represented by nucleotide numbers 186–282, nucleotide numbers 127–282 or nucleotide numbers 1–282 within the nucleotide sequence shown by SEQ ID:No.3.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE INVENTION

Figure 1:
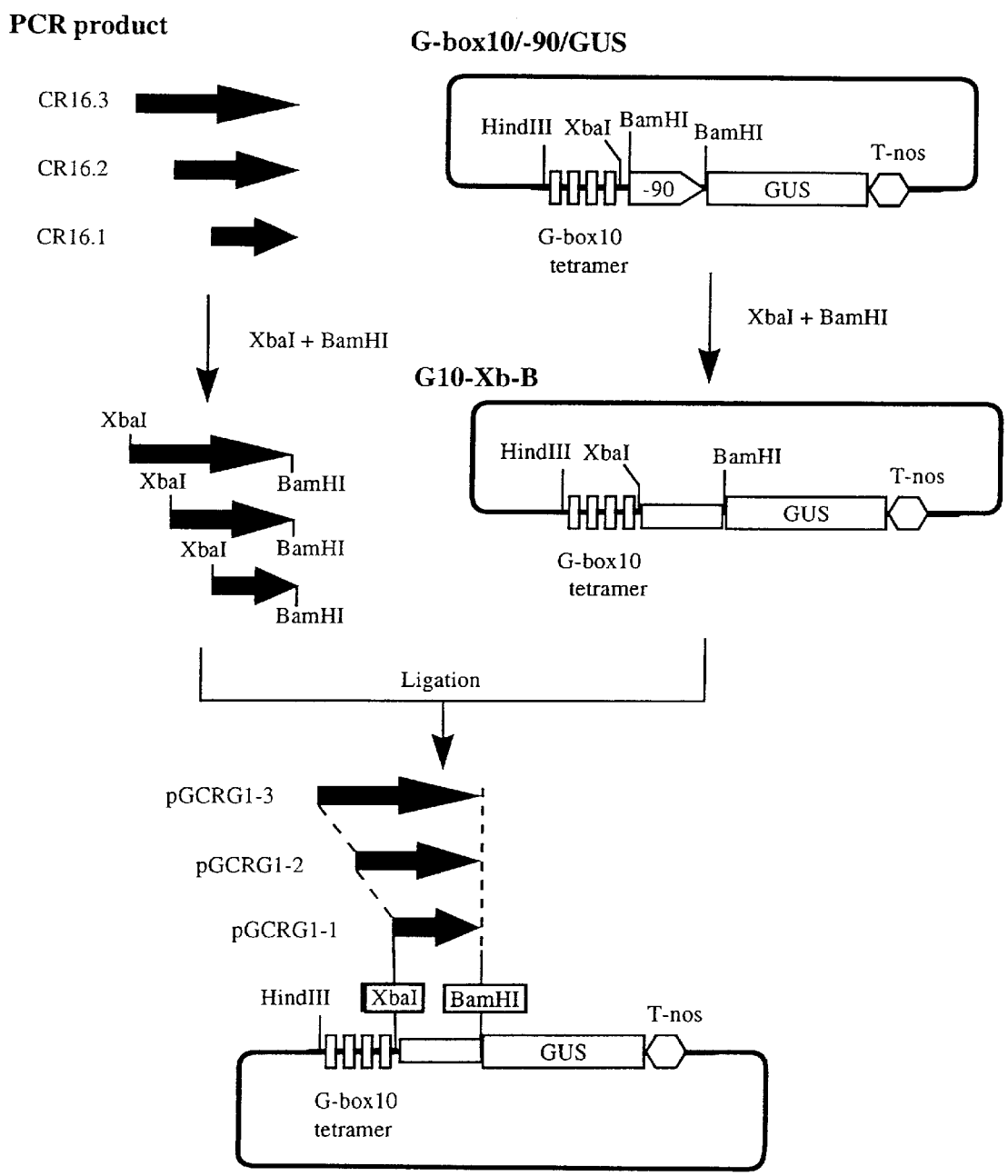
FIG. 1 is a view showing a step for constructing the plasmids pGCRG1-1, pGCRG1-2 and pGCRG1-3 containing the present promoter. In the figure, GUS denotes β-glucuronidase gene, and T-nos denotes a terminator of nopaline synthase gene derived from Ti-plasmid.

The present invention will be described in detail below.

The genetic engineering technique used here can be performed in accordance with a conventional method described in, for example, Molecular Cloning $2^{nd}$ edition authored by J. Sambook, E. F. Frisch and T. Maniatis, (published by Cold Spring Harbor Laboratory press, 1989), DNA cloning authored by M. Glover (published by IRL, 1985) and the like.

The present promoter is a promoter having the following DNA sequence (a) or (b) and a DNA having the nucleotide sequence shown by SEQ ID:No.1,
  (a) a DNA sequence having the nucleotide sequence represented by at least nucleotide numbers 112–246 within the nucleotide sequence shown by SEQ ID:No.2,
  (b) a DNA sequence having the nucleotide sequence represented by at least nucleotide numbers 186–282 within the nucleotide sequence shown by SEQ ID:No.3.

As the "a DNA sequence having the nucleotide sequence represented by at least nucleotide numbers 112–246 within the nucleotide sequence shown by SEQ ID:No.2" (hereinafter referred to as DNA sequence A), there are the nucleotide sequence represented by nucleotide numbers 112–246, the nucleotide sequence represented by nucleotide numbers 54–246, the nucleotide sequence represented by nucleotide numbers 1–246 of the nucleotide sequence shown by SEQ ID:No.2 and the like. In addition, as the "a DNA sequence having the nucleotide sequence represented by at least nucleotide numbers 186–282 within the nucleotide sequence shown by SEQ ID:No.3" (hereinafter referred to as DNA sequence B), there are the nucleotide sequence represented by nucleotide numbers 186–282, the nucleotide sequence represented by nucleotide numbers 127–282, the nucleotide sequence represented by nucleotide numbers 1–282 of the nucleotide sequence shown by SEQ ID:No. 3 and the like.

It is preferable that the above sequence shown by SEQ ID:No.1 is usually positioned 5' upstream of above DNA sequence A or the DNA sequence B and, as a distance between a DNA having the nucleotide sequence shown by SEQ ID:No.1 and the DNA sequence A or B is shorter, a compact promoter having the shorter sequence can be constructed.

The present promoter may have two or more than two copies of the nucleotide sequence shown by SEQ ID:No.1. For example, there are promoters having, preferably 4 or 8 tandem repeats of the nucleotide sequence shown by SEQ ID:No.1. The other nucleotide sequence may intervene between the nucleotide sequences shown by SEQ ID:No.1. However, since when the other nucleotide sequence intervenes therebetween, a length of a promoter becomes longer, the nucleotide sequences are preferably tandemly connected without any other nucleotide sequences. Here, "tandem repeats" means that two or more than two nucleotide sequences having the same nucleotide sequences are connected to each other successively.

The present promoter may be prepared by separately preparing the DNA sequence A or the DNA sequence B and a DNA having the nucleotide sequence shown by SEQ ID:No.1, according to methods of the conventional chemical synthesis and in vitro annealing, and ligating the separately obtained DNAs, respectively, according to a method using, for example, DNA ligase or the like.

More particularly, a DNA fragment having the nucleotide sequence represented by nucleotide numbers 112–246 of the nucleotide sequence shown by SEQ ID:No.2 may be prepared by, for example, chemically synthesizing a nucleotide (+chain) shown by SEQ ID:No:6 and its complementary nucleotide (−chain) shown by SEQ ID:No.7, and annealing them in vitro. On the other hand, a DNA fragment having 4 tandem repeats of the nucleotide sequence shown by SEQ ID:No.1 may be prepared by chemically synthesizing an oligonucleotide (+chain) having the nucleotide sequence shown by SEQ ID:No.4 and its complementary oligonucleotide (−chain) having the nucleotide sequence shown by SEQ ID:No.5 and annealing them in vitro. The present promoter may be prepared by ligating a DNA fragment having 4 tandem repeats of the nucleotide sequence shown by SEQ ID:No.1 5' upstream to thus obtained DNA fragment having the nucleotide sequence represented by nucleotide numbers 112–246 of the nucleotide sequence shown by SEQ ID:No.2 using T4 DNA ligase (Takara Shuzo Co., Ltd.).

Similarly, a DNA fragment having 8 tandem repeats of the nucleotide sequence shown by SEQ ID:No. 1 may be prepared by chemically synthesizing an oligonucleotide (+chain) having 8 tandem repeats of the nucleotide sequence shown by SEQ ID: No. 1 and its complementary sequence (−chain) and annealing them in vitro. The present promoter may be prepared by ligating a DNA fragment having the nucleotide sequence in which 8 tandem repeats of the nucleotide sequence shown by SEQ ID:No.1 5' upstream to thus obtained DNA fragment having the nucleotide sequence represented by nucleotide numbers 112–246 of the nucleotide sequence shown by SEQ ID:No.2 using T4 DNA ligase (Takara Shuzo Co., Ltd.).

Alternatively, the present promoter may be prepared by, for example, cloning a gene from the tissues or cells previously known to have the gene containing the desired DNA fragment, excising either of or both of a DNA fragment having the DNA sequence A or the DNA sequence B and a DNA fragment having the nucleotide sequence shown by SEQ ID:No.1 using a suitable restriction enzyme and ligating the resulting DNA fragments using a method employing a DNA ligase or the like as necessary.

Alternatively, the present promoter may be prepared by performing PCR (polymerase chain reaction) to obtain either of or both of a DNA fragment having the DNA sequence A or the DNA sequence B and a DNA fragment having the nucleotide sequence shown by SEQ ID:No.1 using the gene cloned as described above as a template and using primers to amplify the DNA fragments, and ligating the resulting DNA fragments using a method employing a DNA ligase or the like as necessary.

More particularly, a DNA fragment comprising the nucleotide sequence shown by SEQ ID:No.2 may be obtained by, for example, performing PCR using as a primer an oligonucleotide having the nucleotide sequence represented by nucleotide numbers 1–20 in the nucleotide sequence shown by SEQ ID:No.2 and an oligonucleotide having the nucleotide sequence complementary to the nucleotide sequence represented by nucleotide numbers 226–246 in the nucleotide sequence shown by SEQ ID:No.2 and using a carrot genomic DNA as a template.

Similarly, a DNA fragment comprising the nucleotide sequence shown by SEQ ID:No.3 may be obtained by, for example, performing PCR using as a primer an oligonucleotide having the nucleotide sequence represented by nucleotide numbers 1–20 in the nucleotide sequence shown by SEQ ID:No.3 and an oligonucleotide having the nucleotide sequence complementary to the nucleotide sequence represented by nucleotide numbers 262–282 in the nucleotide sequence shown by SEQ ID:No.3 and using a soybean genomic DNA as a template. Thus obtained DNA fragments may be ligated with the DNA fragment having the nucleotide sequence shown by SEQ ID:No.1, which was prepared by chemical synthesis and annealing in vitro as described above, to prepare the present promoter.

A copy number of the nucleotide sequence shown by SEQ ID: No.1 in the present promoter may be varied by performing PCR using a DNA containing the present promoter made as described above as a template and using a primer containing the nucleotide sequence shown by SEQ ID:No.1. For example, the present promoter with increased copy number of the nucleotide sequence shown by SEQ ID:No.1 may be prepared by using the plasmid pGCRG1-1 or pGCRG1-2 containing the present promoter as a template and using as a primer an oligonucleotide selectively having the nucleotide sequence (SEQ ID:No.18 or SEQ ID:No.19) containing two or more than two, for example, 8 tandem repeat of the nucleotide sequence shown by SEQ ID:1 and a primer having the nucleotide sequence complementary to a region located 3' downstream of the present promoter in a template plasmid, for example, an oligonucleotide having the nucleotide sequence shown by SEQ ID:20.

The desired gene can be expressed in a host cell by using thus obtained present promoter. In this case, a chimera gene having the present promoter and the desired gene (hereinafter referred to as the present chimera gene) may be utilized. Here, "the desired gene" is a gene which is desired to be expressed in a host cell and an example thereof is a gene encoding an enzyme, a storage protein, a receptor, a transcription regulating factor, a signal transmitting factor or the like, and these genes may be ligated downstream of the present promoter in a sense direction or an anti-sense direction depending upon the object of present invention. The present chimera gene may contain a terminator functional in a host cell as necessary. The terminator functional in a host cell is not limited to specified ones as long as it shows the termination activity in a host cell to be transformed and, in a case where a host cell is a plant cell, there are a terminator (NOS) of the nopaline synthase gene derived from the Ti-plasmid of Agrobacterium genus, a terminator derived from a plant virus such as garlic virus GV1, GV2 and the like. It is preferred that, in the present chimera gene, the present promoter and the desired gene are usually ligated in a functional form. "In a functional form" herein means that, upon introduction of the present chimera gene to transform a host cell, the desired gene contained in the chimera gene is ligated to the present promoter and, if necessary to the terminator such that the desired gene is expressed under the control of the present promoter and, if necessary, the terminator.

In a vector having the present promoter, a vector is a DNA which can be replicated in a host cell and examples thereof are a plasmid, phage, phagemid and the like which can amplify in a host cell such as *E. coli*, yeast, plant cell, animal cell and the like. More particularly, there are pUC plasmid [pUC118, pUC119 (Takara Shuzo Co., Ltd.) and the like], pSC101 plasmid, Ti-plasmid [pBI101, pBI121 (CLONTECH Co.) and the like], Bluescript phargemid [pBluescript SK(+/-) (STRATAGENE Co.) and the like], M13 phage [mp10, mp11 (Amersham Co.) and the like], λ phage [λ gt 10, gt 11 (Amersham Co.) and the like], cosmids [SuperCosi (STRATAGENE Co.) and the like] and the like, and a vector having the present promoter may be constructed by cloning the present promoter into such the vector using the conventional genetic engineering techniques.

When a vector having the present promoter has further a cloning site and a terminator functional in a host cell, which is positioned 3' downstream of the promoter, this vector may be preferably utilized for constructing a vector for expressing the desired gene in a host cell. "Cloning site" herein is a nucleotide sequence which can be specifically recognized and cleaved by a restriction enzyme usually used in the genetic engineering techniques and a restriction enzyme recognition sequence which is uniquely present on a vector is preferable. It is preferable that such the cloning site, the present promoter and the terminator functional in a host cell are positioned such that the present promoter, the desired gene and the terminator functional in a host cell are functionally ligated on the vector upon insertion of the desired gene into the cloning site. In order to construct such a vector, a DNA fragment having the nucleotide sequence shown by SEQ ID:No.1, and a DNA fragment having the nucleotide sequence represented by at least nucleotide numbers 112–246 within the nucleotide sequence shown by SEQ ID:No.2 or the nucleotide sequence represented by nucleotide numbers 186–282 within the nucleotide sequence shown by SEQ ID:No.3 may be inserted into a multicloning site of a plasmid containing the cloning site and a terminator functional in a host cell, more particularly, pBI101.3 (manufactured by CLONTECH Co.). Alternatively, the present promoter and a terminator functional in a host cell may be inserted into a multicloning site of a vector, more particularly, pBIN19 (Nuc. Acid. Res. 12:8711–8721(1984)) and the like.

A vector having the present chimera gene is suitable for introduction of the chimera gene into a host cell, and may be prepared, for example, by cloning the chimera gene into the aforementioned vector or cloning the desired gene into a cloning site of the aforementioned vector having the present promoter, the cloning site and a terminator functional in a host cell. A vector having the present chimera gene may be prepared by removing a reporter gene (β-gluclonidase gene; hereinafter expressed as GUS gene) present on the aforementioned vector by cleaving the vector derived from, for example, pBOI101.3 (manufactured by CLONTECH Co.) by using a suitable restriction enzyme, inserting the desired gene in place of the reporter gene.

The present vector may be introduced into a host cell derived from a micro organism such as *E. coli*, Agrobacterium or the like by a calcium chloride method, an electroporation method and the like described in, for example, J., Sambrook, E. F., Frisch, authored by T. Maniatis, Molcecular Cloning, 2nd edition (1989) (published by Cold Spring Harbor Laboratory), further and a host cell into which the present vector was introduced is useful for preparation of the present chimera gene and introduction of the present chimera gene into other host cell.

Alternatively, the present promoter may be introduced into a host cell derived from a plant by a particle bombardment method and the like. Alternatively, the present vector may be introduced into a host cell derived from a plant by the known method such as an Agrobacterium infection method, an electroporation method, a particle bombardment method or the like.

As a plant into which the present promoter, the present chimera gene or the present vector may be introduced to express the desired gene in a host cell under the control of the present promoter, there are monocotyledon such as rice, maize, barley, wheat and the like, dicotyledon plant such as Leguminosae plant such as soybean, garden pea, Phaseolus, alfalfa and the like, Solanaceae plant such as tobacco, tomato, potato and the like, Brassica plant such as cabbagy, rapeseed, mustard and the like, Cucurbitaceae plant such as melon, pumpkin, cucumber and the like, Umbelliferae plant such as carrot, celery, Compositae plant such as lettuce and the like.

By introducing the present promoter, the present chimera gene or the present vector into a host cell, for example, a transformant in which the present promoter is inserted upstream of the desired gene on the gemomic DNA and which expresses the gene under the control of the present promoter, a transformant in which the present chimera gene is inserted on the genomic DNA and which expresses the desired gene contained in the chimera gene under the control of the present promoter, a transformant which has the present vector in a host cell and expresses the desired gene contained in the vector under the control of the present promoter and the like are obtained.

In order to obtain a transformed plant, a transformed plant cell may be redifferentiated according to a method used in the conventional plant tissue culturing techniques described in, for example, Plant Molecular Biology Manual, Kluwer Academic Publishers press (1988) authored by S. B. Gelvin, R. A. Schiperoot and D. P. S. Verma, Experimental Protocol of Model Plant (Section: Rice, Arabidopsis) (Shurei Co.) (ISBN-4-87962-157-9 C3345, 1996) p.p.78–143 editorially supervisioned by Ko Shimamoto, Kiyotaka Okada or Plant Gene Manupulation Manual, How to make transgenic plant (Kodansha Scientific) 1990, ISBN4-06-153513-7 C3045 p.p.28–33 authored by Hirofumi Uchimiya, to obtain a plant derived from the plant cell or a portion thereof. Further, by cultivating and selfing the plant obtained as described above, a progeny of the plant may be obtained. In the present invention, the transformant includes such the plant cell, plant and progeny.

As described above, a transformant expressing the desired gene in a host cell under the control of the present promoter may be obtained.

The useful trait may be imparted to a host cell by ligating the desired gene in a sense direction and expressing it in a host cell under the control of the present promoter. For example, the protein content and the essential amino acid content in feed crops may be increased by expressing a seed storage protein gene such as soybean glycinin gene, β-conglycinin gene, the methionine or cysteine content in feed crops may be increased by expressing a gene encoding a storage protein containing high methionine or cysteine such as the Barazil nuts 2S albumin gene, maize γ-zein gene and the like, the biotin content may be increased in feed crops by expressing a biotin biosynthesis-related enzyme gene such as bioA, bioB, bioC, bioF, bioH enzyme genes derived from a microorganism such as *E. coli*, a starch component in a rice seed may be altered by expressing a amylopectin synthesis-related enzyme gene such as rice α-1,4-glucan branching enzyme and the like, the improvement of lipid components by the promotion in the oxidation stability of a lipid, the decrease in a phospholipid and the increase in oleic acid and linolenic acid in edible crops becomes possible by expressing the soybean or rapeseed stearoyl-ACP-desaturase gene, acyl-ACP-thioesterase gene, the coconut 1-acylglycerol-3-phosphate acyl transferase gene and the like, and the unsaturated fatty acid content may be increased or the resistance to low temperature of a plant may be increased by expressing the spinach glycerol-3-phosphate acyltransferase gene and the like.

On the other hand, the useful trait may be imparted to a host cell by placing the desired gene in an anti-sense direction and expressing in a host cell under the control of the present promoter. For example, a starch component in a rice seed may be improved by expressing an anti-sense gene of amylopectin degrading enzyme gene such as the rice isomerase, the storage properties of fruit, flower and the like may be improved by expressing an anti-sense gene of the ethylene synthesizing enzyme gene such as pumpkin 1-aminocyclopropane-1-carboxylate (ACC) synthase and the like, and the storage properties of fruit may be improved by expressing an anti-sense gene of the tomato polygalacturonase gene.

Further, the fertility of a plant may be controlled by expressing a sense or anti-sense gene of a male sterility-related gene such as S-locus type specific RNase gene involved in the plant self incompatibility.

The present invention will be explained in more detail by way of Examples but is not limited to them.

EXAMPLE 1 (Construction of GUS expression plasmid)

After 2 μg of the plasmid Gbox10/-90/GUS(described in JP-A-9-131187) was digested with restriction enzymes XbaI and BamHI, the digested fragments were separated by 0.8% agarose gel electrophoresis, and about 12 kbp DNA fragments (hereinafter referred to as G10-Xb-B fragment) were isolated and purified using a DNA purification kit (Prep-A-Gene DNA Purification Systems, manufactured by BIO-RAD). Similarly, after 2 μg of the plasmid -90/GUS (described in JP-A-9-131187) was digested with restriction enzymes XbaI and BamHI, the digested fragments were separated by 0.8% agarose gel electrophoresis, and about 12 kbp DNA fragments (hereinafter referred to as Xb-B fragment) were isolated and purified.

On the other hand, oligonucleotides having the nucleotide sequence shown by SEQ ID:Nos. 8–15 were synthesized using a DNA synthesizer (Applied Biosystems). A 150 bp DNA fragment (hereinafter referred to as CR16.1 fragment) having the nucleotide sequence represented by nucleotide numbers 112–246 within the nucleotide sequence shown by SEQ ID: No.2 was prepared by performing PCR using the plasmid pCR16G1/Xb (described in JP-A-8-212680) as a template and using an oligonucleotide having the nucleotide sequence shown by SEQ ID:No. 8 and an oligonucleotide having the nucleotide sequence shown by SEQ ID:No. 9 as a primer. Similarly, a 208 bp DNA fragment (hereinafter referred to as CR16.2 fragment) having the nucleotide sequence represented by nucleotide numbers 54–246 within the nucleotide sequence shown by SEQ ID: No.2 was prepared by performing PCR using an oligonucleotide having the nucleotide sequence shown by SEQ ID:No. 8 and an oligonucleotide having the nucleotide sequence shown by SEQ ID:No. 10 as a primer, and a 268 bp DNA fragment (herinafter referred to as CR16.3 fragment) having the nucleotide sequence shown by SEQ ID: No.2 was prepared by performing PCR using an oligonucleotide having the nucleotide sequence shown by SEQ ID:No. 8 and an oligonucleotide having the nucleotide sequence shown by SEQ ID:No. 11 as a primer. On the other hand, a 110 bp DNA fragment (referred to as GY1.1 fragment) having the nucleotide sequence represented by nucleotide numbers 186–282 within the nucleotide sequence shown by SEQ ID:No.3 was prepared by performing PCR using the plasmid pGY1 (Iida et al., Plant Cell Report 14:539–544 (1995)) as a template and using an oligonucleotide having the nucleotide sequence shown by SEQ ID:No. 12 and an oligonucleotide having the nucleotide sequence shown by SEQ ID:No. 13 as a primer. Similarly, a 170 bp DNA fragment (referred to as GY1.2 fragment) having the nucleotide sequence represented by nucleotide numbers 127–282 within the nucleotide sequence shown by SEQ ID:No.3 was prepared by performing PCR using an oligonucleotide having the nucleotide sequence shown by SEQ ID:No. 12 and an oligonucleotide having the nucleotide sequence shown by SEQ ID:No. 14 as a primer, and a 296 bp DNA fragment (referred to as GY1.3 fragment) having the nucleotide sequence shown by SEQ ID:No.3 was prepared by performing PCR using an oligonucleotide having the nucleotide sequence shown by SEQ ID:No. 12 and an oligonucleotide having the nucleotide sequence shown by SEQ ID:No. 15 as a primer. The PCRs described above were all performed using TAKARA Taq polymerase (Takara Shuzo Co., Ltd.) in a reaction solution comprising 10 mM Tris-HCl pH 8.0, 50 mM KCl, 0.2 mM dNTP mixture solution (each containing each cycle comprising temperature maintaining at 94° C. for 1 minutes, then at 55° C. for 2 minutes, and at 72° C. for 3 minutes. Each 1 μg of the amplified DNA fragment was digested with restriction enzymes Xbal and BamHI.

Figure 2:
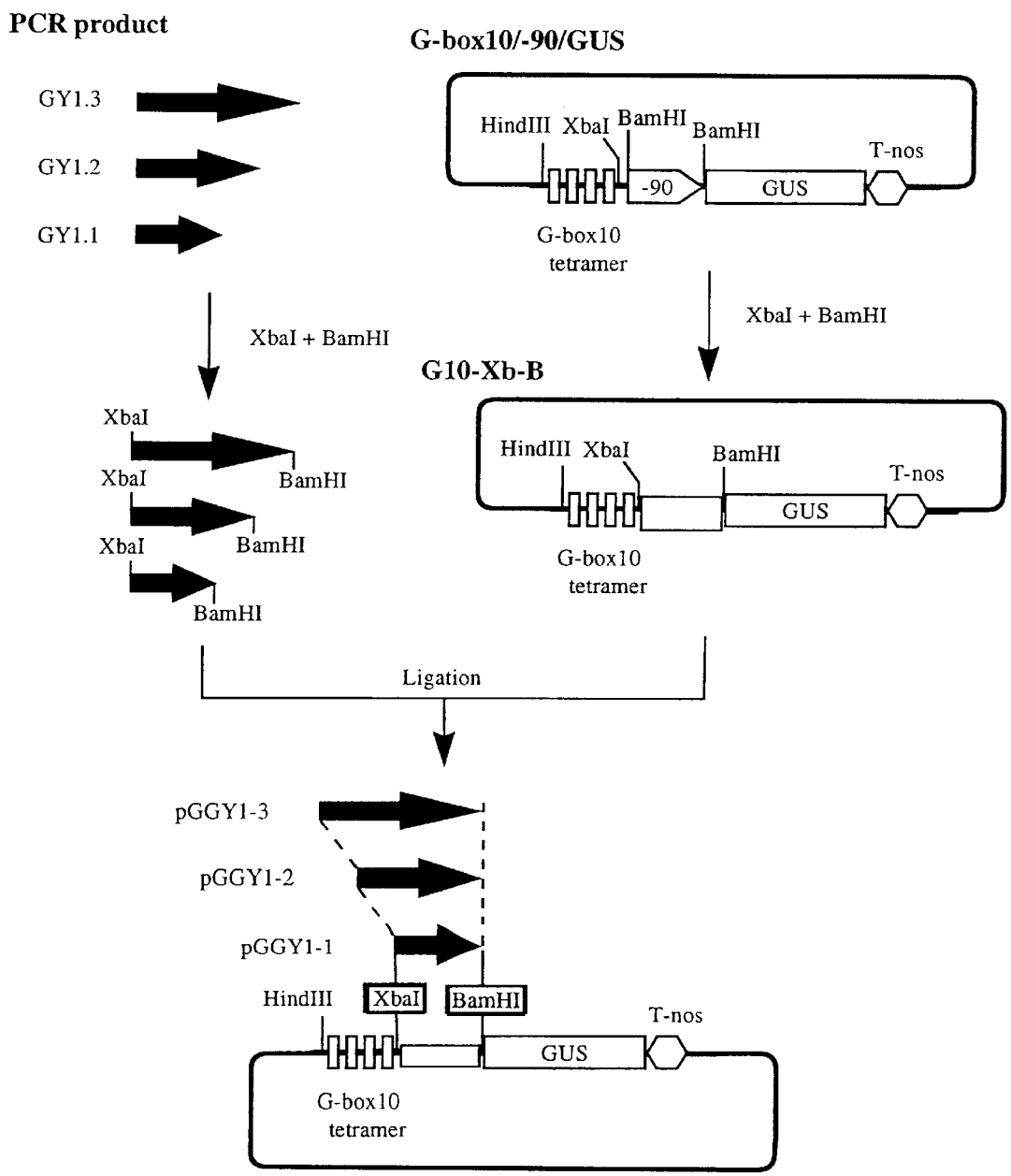
FIG. 2 is a view showing a step for constructing the plasmid pGGY1-1, pGGY1-2 and pGGY1-3 containing the present promoter. In the figure, GUS denotes β-glucuronidase gene and T-nos denotes a terminator of nopaline synthase gene derived from Ti-plasmid.
Figure 3:
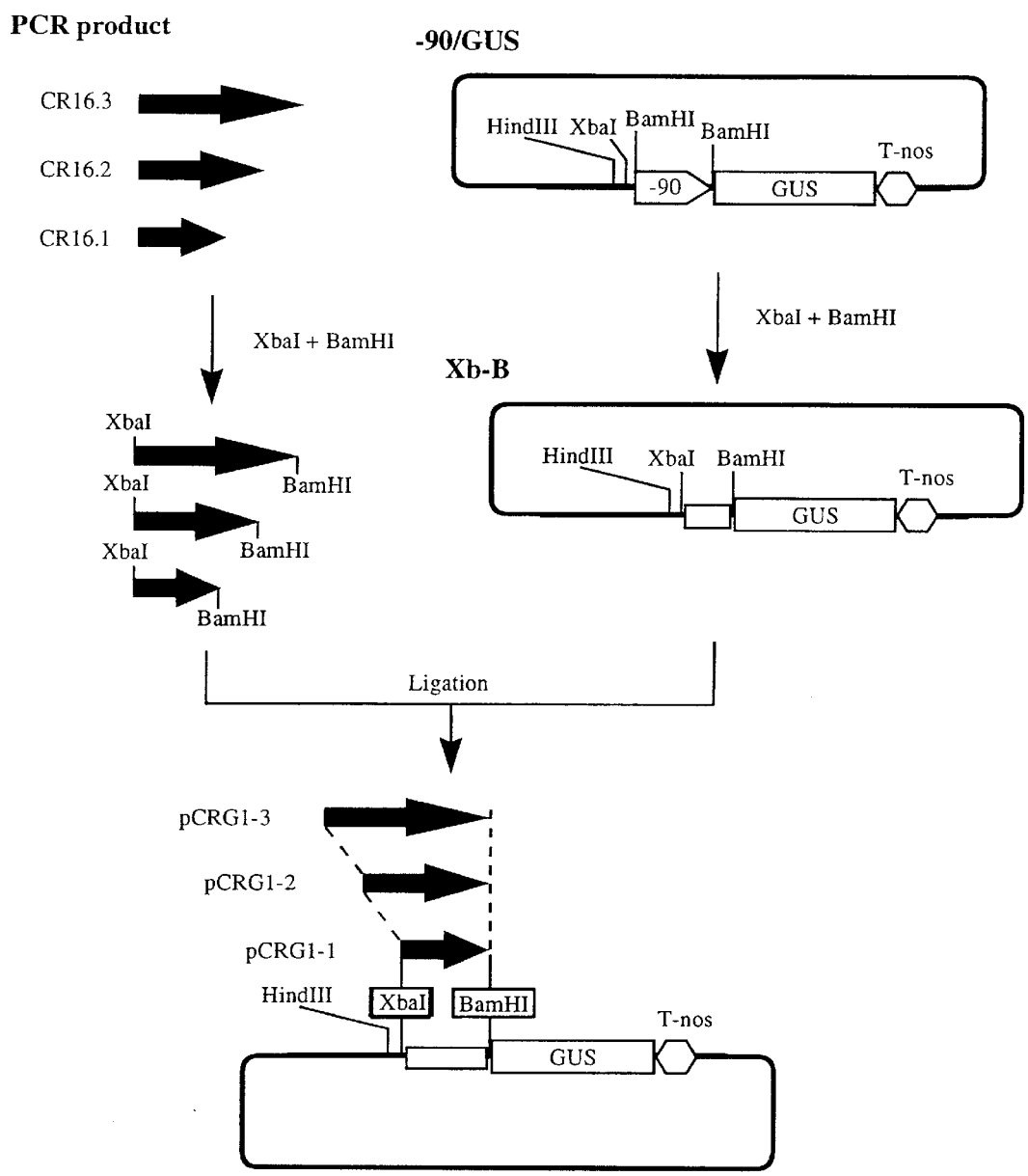
FIG. 3 is a view showing a step for constructing the plasmid pCRG1-1, pCRG1-2 and pCRG1-3. In the figure, GUS denotes β-glucuronidase gene and T-nos denotes a terminator of nopaline synthase gene derived from Ti-plasmid.
Figure 4:
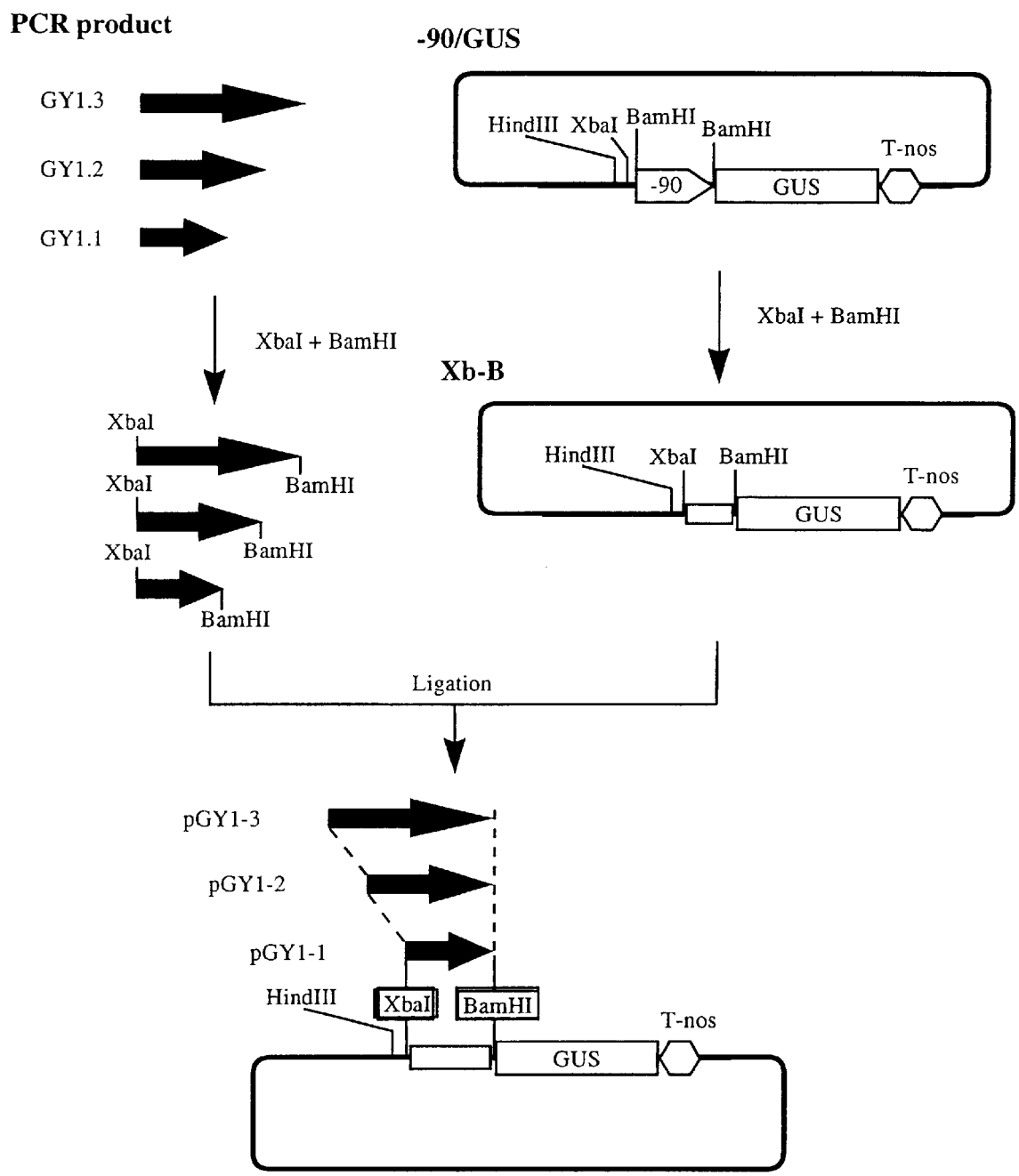
FIG. 4 is a view showing a step for constructing the plasmid pGY1-1, pGY1-2 and pGY1-3. In the figure, GUS denotes β-glucuronidase gene and T-nos denotes a terminator of nopaline synthase gene derived from Ti-plasmid.

Each 0.2 μg of thus obtained DNA fragment was mixed with 2 μg of above G10-Xb-B fragment and 2 μg of Xb-B fragment, respectively, and ligated using the ligation kit version 2 (manufactured by Takara Shuzo Co., Ltd.), which was introduced into E. coli strain HB101 (manufactured by Takara Shuzo Co., Ltd.). CR16.1 fragment, CR16.2 fragment or CR16.3 fragment was ligated with G10-Xb-B fragment, respectively, to construct the plasmid pGCRG1-1, pGCRG1-2 or pGCRG1-3 (FIG. 1). The plasmid pGGY1-1, pGGY1-2 or pGGY1-3 were constructed by ligating GY1.1 fragment, GY1.2 fragment or GY1.3 fragment with G10-Xb-B fragment, respectively (FIG. 2). The plasmid pCRG1-1, pCRG1-2 or pCRG1-3 were constructed by ligating CR16.1 fragment, CR16.2 fragment or CR16.3 fragment with Xb-B fragment, respectively (FIG. 3). The plasmid pGY1-1, pGY1-2 or pGY1-3 were constructed by ligating GY1.1 fragment, GY1.2 fragment or GY1.3 fragment with Xb-B fragment, respectively (FIG. 4).

Figure 5:
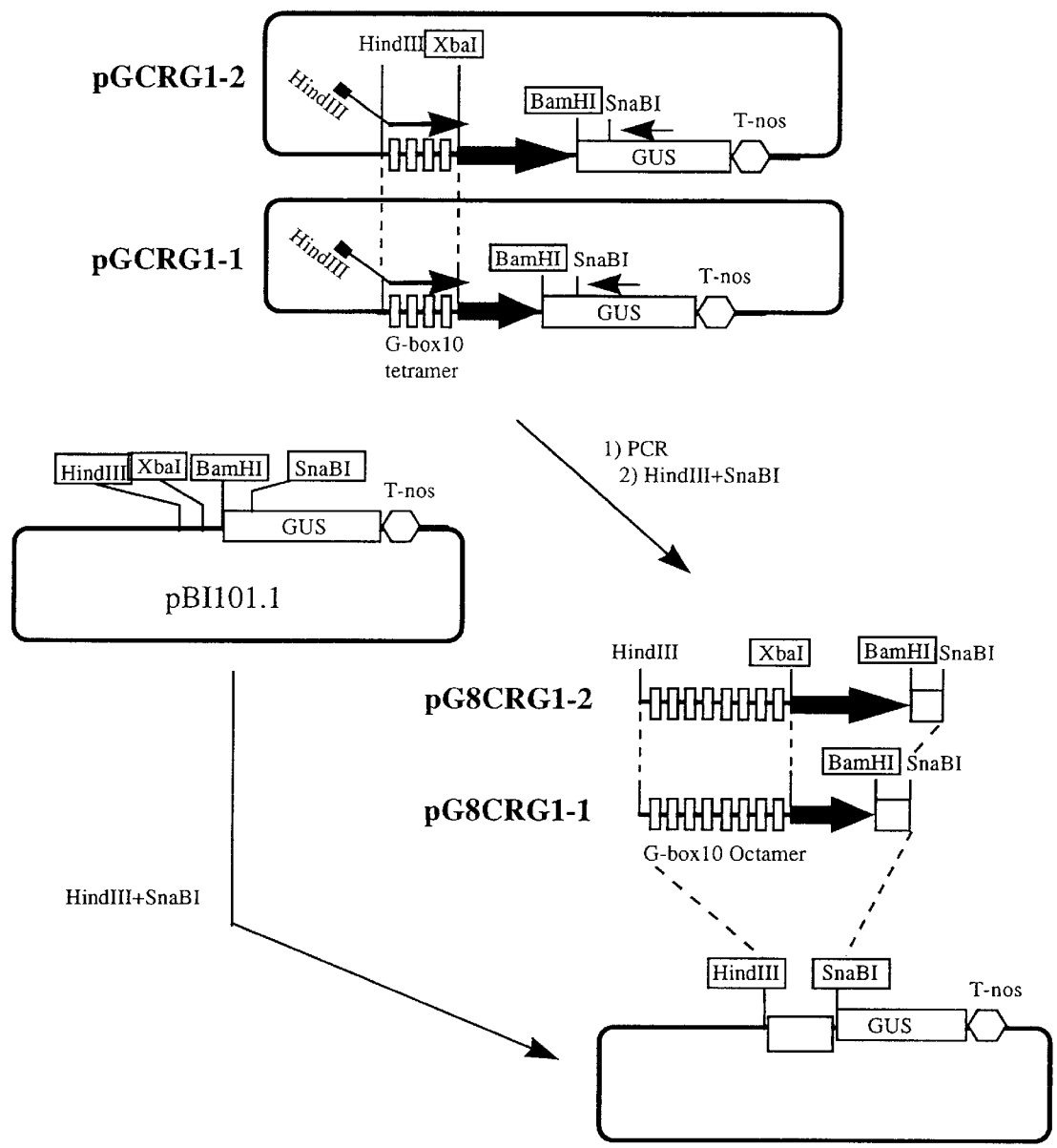
FIG. 5 is a view showing a step for constructing the plasmid pG8CRG1-1, pG8CRG1-2. In the figure, GUS denotes β-glucuronidase gene and T-nos denotes a terminator of nopaline synthase gene derived from Ti-plasmid.

Further, about 630 bp DNA fragment was prepared by performing PCR using the plasmid pCR16G1-1 as a template and using an oligonucleotide having the nucleotide sequence shown by SEQ ID:No.18 and an oligonucleotide having the nucleotide sequence shown by SEQ ID:No.20 as a primer. Similarly, about 690 bp DNA fragment was prepared by perfoiming PCR using pCR 16G1-2 as a template and using an oligonucleotide having the nucleotide sequence shown by SEQ ID:No.19 and an oligonucleotide having the nucleotide sequence shown by SEQ ID:No.20 as a primer. Each of thus obtained DNA fragment was digested with restriction enzymes HindIII and SnaBI. On the other hand, pG8CRG1-1 and pG8CRG1-2 were constructed by ligating the fragments obtained by digesting the plasmid pBI101.1 (manufactured by CLONTECH) with restriction enzymes HindIII and SnaBI and the PCR-amplified DNA fragments (630 bp or 690 bp) digested with HindIII and SnaBI using a T4 DNA polymerase (manufactured by Takara Shuzo Co., Ltd.) (FIG. 5).

EXAMPLE 2 (Preparation of plasmid DNA for gene introduction)

Each E. coli strain HB 101 containing the plasmid pGCRG1-1, pGCRG1-2, pGCRG1-3, pG8CRG1-1, pG8CRG1-2, pGGY1-1, pGGY1-2, pGGY1-3, pCRG1-1, pCRG1-2, pCRG1-3, pGY1-1, pGY1-2 or pGY1-3 obtained in Example 1 was inoculated in 200 ml of L medium containing 50 μg/ml kanamycin and cultured, and each plasmid DNA was purified using the commercially available purification kit (QIAGEN).

EXAMPLE 3 (Production of a transformant by an indirect introducing method)

Each plasmid DNA purified in Example 2 was introduced by heat treatment (37° C. for 5 minutes) into Agrobacterium (Agrobacterium tumefaciens LBA4404) (showing streptomycin resistance and rifampicin resistance) (Hoekma et al. Nature, 303; 179–180 (1983)) which had been competent by trearing with 20 mM CaCl$_2$. Transfornants harboring the kanamycin resistance properties which are imparted by NPTII gene on the plasmids (Trien-Cuot et al., Gene 23:331–341 (1983)) were selected in L agar medium containing 300 μg/ml streptomycin, 100 μg/ml rifampicin and 25 μg/ml kanamycin by culturing Agrobacterium treated with the plasmid.

The resultant transformant of Agrobacterium was cultured overnight at 28° C. in L medium containing 300 μg/ml streptomycin, 100 μg/ml rifampicin and 25 μg/ml kanamycin. The culture of resultant bacterium was used to infect tobacco leaf disks by the conventional method described in Plant Molecular Biology/Manual (1988) (published by Kluwer Academic Publishers) authored by S. B. Gelvin, R. A. Schilperoort the conventional method described in Plant Molecular Biology/Manual (1988) (published by Kluwer Academic Publishers) authored by S. B. Gelvin, R. A. Schilperoort and D. P. S. Verma, and Plant Gene Manupulation Manual, How to make Transgenic Plant (Kodansha Scientific), 1990, ISBN4-06-153513-7 C3045, p.p.28–33 authored by Hirofumi Uchimiya.

After the leaf disks of the tabacco (SR-1) infected with Agrobacterium was cultured in the MS-NB agar medium for 4 days, they were transferred to the MS-NB agar medium containing 500 μg/ml cefotaxime to remove Agrobacterium. At 11 days after infection, they were transferred to the MS-NB agar medium containing 500 μg/ml cefotaxime and 100 μg/ml kanamycin and cultured. After about 4 weeks, a green young plant with stem and leaf differentiated was cut from the leaf disk, implanted on the MS-NB agar medium containing 500 μg/ml cefotaxime and 50 μg/ml kanamycin and selected a rooted young plant. The rooted tobacco young plant was transferred to soil to cultivate in a greenhouse.

EXAMPLE 4 (Confirmation of insertion of introduced gene in transformed plant)

(1) Preparation of genomic DNA from transformed plant

A genomic DNA was prepared from a leaf strip of the transformed plant tobacco obtained in Example 3 using a CTAB method described in Plant Gene Manupulation Manual, How to make Transgenic Plant (Kodansha Scientific), 1990, ISBN4-06-153513-7 C3045) p.p.71–74 authored by Hirofumi Uchimiya. After about 0.5 g of the plant leaf strip was sufficiently ground in Eppendorf tube using a homogenizer, to the leaf homogenate was added 0.5 ml of 2×CTAB solution (2% cetyltrimethyl ammonium bromide, 100 mM Tris-HCl, pH 8.0, 20 mM EDTA, 1.4M NaCl, 1% polyvinylpyrroridone (PVP)) which had previously been maintained at 65° C., which was maintained at 65° C. for 5 minutes. To this was added,0.5 ml of a chloroform/isoamylalcohol (24:1) mixture, which was gently mixed for 5 minutes. The upper layer was taken by centrifuging at 12,000 rpm (10,000×g) for 10 minutes, and ⅒volume of 10% CTAB solution (10% cetyltrimethyl ammonium bromide, 0.7M NaCl) maintained at 65° C. was added thereto, which was maintained at 65° C. for 3 minutes. An equivalent volume of chloroform/isoamylalcohol (24:1) mixture was added to mix well, and the upper layer was taken. Two volumes of CTAB precipitate solution (1% cetyltrimethyl ammonium bromide, 50 mM Tris-HCl, pH 8.0, 10 mM EDTA) was added, which was maintained at 65° C. for 1 minute, centrifuged at 12,000 rpm (10,000×g) to precipitate DNA. The precipitates were dissolved in 50 μl of high salt TE (10 mM Tris-HCl pH 8.0, 1 mM EDTA, 1M NaCl), and 100 μl of ethanol was added to mix. The precipitates which had been obtained by centrifuging at 12,000 rpm (10,000×g) for 15 minutes was dissolved in 50 μl TE (10 mM Tris-HCl pH 8.0, 1 mM EDTA). To this was added RNaseA to 10 μg/ml, which was maintained at 37° C. for 30 minutes, an equivalent volume of phenol/chlorofom/isoamylalcohol (25:24:1) mixture to mix well, and the upper layer was taken. To this were added ⅒volume of 3M sodium acetate (pH 5.2) and 2.5 volume of ethanol to mix well, which was centrifuged at 12,000 rpm (10,000×g) for 5 minutes to recover the precipitates, to obtain about 5 μg of genomic DNA.

(2) Confirmation of insertion of introduced gene by PCR method

PCR (total 30 cycles, each cycle comprising maintaining temperature at 94° C. for 1 minute, then 2 minutes at 55° C., and further 3 minutes at 72° C.) was performed using 50 ng of the genomic DNA obtained in (1) as a template and using an oligonucleotide having the nucleotide sequence shown by SEQ ID:No.16 and an oligonuleotide shown by SEQ ID:17 as a primer. The resultant PCR product was analyzed by 4% agarose gel electrophoresis. As a result, amplification of about 500 bp DNA fragment was observed using tobacco genomic DNA into which the plasmid pGCRG1-1, pGCRG1-2, pGCRG1-3, pG8CRG1-1, pG8CR1-2, pGGY1-1, pGGY1-2, pGGY1-3, pCRG1-1, pCRG1-2, pCRG1-3, pGY1-1, pGY1-2 or pGY1-3 had been introduced, respectively, and the existence of region from 3' terminal of GUS gene coding region to the terminator of nopaline synthase gene (NOS).

EXAMPLE 5 (Self-fertilization of transformant and development of genetically homogous line)

The transformed tabacco, the existence of the introduced gene of which was confirmed in Example 4, was transferred to soil, and cultivated in a greenhouse. At the time of anthesis (flowering), plants were self-pollinated and seeds were obtained from matured flowers. The resultant seeds were sterilized in 1% sodium hypochlorite for 5 minutes, and seeded on MS agar medium containing 100 μg/ml kanamycin. A clone in which about ¾ of the seeded seeds were germinated to growth was selected. The selected seed was seeded again on MS agar medium containing 100 μg/ml kanamycin, and a clone in which whole seeds were germinated was selected, which was used for the following experiment.

EXAMPLE 6 (Expression of GUS gene in each tissue of transformant)

After the transformed tabacco seeds obtained in Example 5 (containing T-DNA region of the plasmid pGCRG1-1, pGCRG1-2, pGCRG1-3, pG8CRG1-1, pG8CRG1-2, pGGY1-1, pGGY1-2, pGGY1-3, pCRG1-1, pCRG1-2, pCRG1-1, pCRG1-3, pGY1-1, pGY1-2, or pGY1-3) and, as a control, untransformed tabacco SR-1 seed were sterilized in 1% sodium hypochlorite for 5 minutes, they were seeded on MS agar medium containing 100 μl/ml kanamycin or MS agar medium (in a case of SR-1 seed) and cultivated for about 2 weeks to obtain a seedling.

About 200 mg of leaf and root of the resultant seedling (young plant) were ground using a pestle and a mortar in 300 μl of extraction buffer, and centrifuged at 12,000 rpm (10,000×g). The resultant supernatant was used for measuring the GUS activity. A reaction solution obtained by adding 100 μl of 5 nM 4-methyl-umbelliferyl-D-glucronide (MUG) to 400 μl of extraction buffer was maintained at 37° C. and 10 μl of the supernatant was added. 100 μl of the reaction solution was taken at every 15 minutes, and the reaction was stopped by the addition of 900 μl of 0.2M calcium carbonate. The fluorescence of the sample thus obtained with time was measured using a fluorometer. The fluorescence analysis was performed at 365 nm excition and 455 nm emission and 0–50 ng/ml concentration of 4-methyl-umbelliferone (4-MU) was used as a standard. The protein content in the extraction solution of each plant sample was measured using Protein Assay Kit (Bio Rad) and specific activity per protein was calculated. The results of measured GUS activity of cotyledon, root and seed of each of 10 transformed tabacco lines with the present plasmid introduced and untransformed tabacco SR-1 used as a control are shown in Table 1.

In addition, each transformed tabacco was transferred to soil and cultivated in a greenhouse. Pollen was obtained from flowers at the time of anthesis. Regarding a seed and pollen of each of 5 transformed tabacco lines and untransformed tabacco SR-1 used as a control, expression of the GUS gene was examined according to a staining method described in Plant Gene Manupulation Manual, How to make Transgenic Plant (Kodansha Scientific), 1990, ISBN4-06-153513-7 C3045 p.p.68–70 authored by Hirofumi Uchimiya and Plant Mol. Biol. Rep. 5:387–405 (1987) authored by by Jefferson. The results are shown in Table 2.

TABLE 1

| GUS specific activity in various tissues | | | |
|---|---|---|---|
| | GUS Specific Activity | | |
| Introduced Plasmid | Seed | Leaf | Root |
| pCRG1-1 | – | – | – |
| pGCRG1-1 (Present Invention) | ++++ | + | + |
| pCRG1-2 | – | – | – |
| pGCRG1-2 (Present Invention) | ++++ | + | + |

TABLE 1-continued

GUS specific activity in various tissues

| Introduced Plasmid | GUS Specific Activity | | |
|---|---|---|---|
| | Seed | Leaf | Root |
| pCRG1-3 | − | − | + |
| pGCRG1-3 (Present Invention) | ++++ | + | ++ |
| pG8CRG1-1 (Present Invention) | ++++ | +++ | + |
| pG8CRG1-2 (Present Invention) | +++++ | +++ | ++ |
| pGY1-1 | − | − | − |
| pGGY1-1 (Present Invention) | ++++ | + | − |
| pGY1-2 | − | − | − |
| pGGY1-2 (Present Invention) | ++++ | + | − |
| pGY1-3 | ++ | − | − |
| pGGY1-3 (Present Invention) | ++++ | + | − |
| -(Control) | − | − | − |

-(Control): Untransformed tobacco SR-1
Number of +: showing the highness of the GUS specific activity

TABLE 2

GUS stainability in seed and pollen

| Introduced Plasmid | GUS Stainability | |
|---|---|---|
| | Seed | Pollen |
| pCRG1-1 | − | − |
| pGCRG1-1 (Present Invention) | +++ | ++++ |
| pGCRG1-2 | − | − |
| pCRG1-2 | ++++ | ++++ |
| pCRG1-3 | − | + |
| pGCRG1-3 (Present Invention) | +++ | + |
| pGY1-1 | − | − |
| pGGY1-1 (Present Invention) | ++++ | +++ |
| pGY1-2 | − | − |
| pGGY1-2 (Present Invention) | ++++ | ++ |
| pGY1-3 | ++ | − |
| pGGY1-3 (Present Invention) | ++++ | − |

-(Control): Untransformed tobacco SR-1
Highness of staining: ++++ (Particularly dense), +++ (Dense), ++ (Intermediately dense), + (Dilute), − (No)

Compositions of the media used in Examples are shown below.

MS Agar Medium 34.7 g of MURASHIGE AND SKOOG (Flow Laboratories) was dissolved in 1 L of distilled water, which was adjusted to pH 5.8 with 1 M KOH, 8 g of agar was added thereto, and sterilized by autoclaving.

MS-NB Agar Medium

A medium with 0.1 mg/mL of 1-naphthaleneacetic acid (NAA) and 1.0 mg/mL of 6-benzylaminopurine (BA) added L Medium 10 g of bactotrypton (Dfcio), 5 g of bactoyeast extract (Difco), and 10 g of NaCl were dissolved in 1 L of distilled water, adjusted to pH 7.0 with 5M NaOH, and sterilized by autoclaving.

Reaction Extraction Solution for Measuring GUS Activity.

Solution containing 50 mM phosphate buffer (pH 7.0), 10 mM EDTA, 0.1% Triton X-100, 0.1% sarkosyl, and 10 mM 2-mercaptoethanol.

According to the present invention, there becomes possible to provide a compact promoter suitable for more highly expressing the desired gene in the particular tissue than in other tissues in a host.

What is claimed is:

1. An isolated promoter comprising DNA sequence (a) or (b) and a DNA having the nucleotide sequence shown by SEQ ID:No.1, wherein
   (a) is a DNA sequence having the nucleotide sequence represented by at least nucleotide numbers 112–246 within the nucleotide sequence shown by SEQ ID:No.2, and
   (b) is a DNA sequence having the nucleotide sequence represented by at least nucleotide numbers 186–282 within the nucleotide sequence shown by SEQ ID:No.3.

2. An isolated promoter comprising DNA sequence (a) or (b) and a DNA having the nucleotide sequence shown by SEQ ID:No.1, wherein
   (a) is a DNA sequence represented by nucleotide numbers 112–246, nucleotide numbers 54–246 or nucleotide numbers 1–246 within the nucleotide sequence shown by SEQ ID:No.2, and
   (b) is a DNA sequence represented by nucleotide numbers 186–282, nucleotide numbers 54–246 or nucleotide numbers 1–246 within the nucleotide sequence shown by SEQ ID:No.3.

3. The promoter according to claim 1 or 2, wherein the nucleotide sequence shown by SEQ ID:No.1 is positioned 5' upstream of the DNA sequence (a) or (b).

4. The promoter according to claim 1 or 2, comprising two or more copies of the nucleotide sequence shown by SEQ ID:No.1.

5. The promoter according to claim 4, comprising 4 or 8 copies of the nucleotide sequence shown by SEQ ID:No.1.

6. A chimeric gene comprising an isolated promoter comprising DNA sequence (a) or (b) and a DNA having the nucleotide sequence shown by SEQ ID:No.1, wherein
   (a) is a DNA sequence having the nucleotide sequence represented by at least nucleotide numbers 112–246 within the nucleotide sequence shown by SEQ ID:No.2, and
   (b) is a DNA sequence having the nucleotide sequence represented by at least nucleotide numbers 186–282 within the nucleotide sequence shown by SEQ ID:No.3,
   and a desired gene.

7. A vector comprising an isolated promoter comprising DNA sequence (a) or (b) and a DNA having the nucleotide sequence shown by SEQ ID:No.1, wherein
   (a) is a DNA sequence represented by nucleotide numbers 112–246, nucleotide numbers 54–246 or nucleotide numbers 1–246 within the nucleotide sequence shown by SEQ ID:No.2, and
   (b) is a DNA sequence represented by nucleotide numbers 186–282, nucleotide numbers 54–246 or nucleotide numbers 1–246 within the nucleotide sequence shown by SEQ ID:No.3.

8. The vector according to claim 7, further comprising a cloning site and a terminator functional in a host cell, which is positioned 3' downstream of the promoter.

9. A vector comprising the chimeric gene of claim 6.

10. A transformant wherein the promoter according to claim 1 or 2, is introduced into a host cell.

11. The transformant according to claim 10, wherein the host cell is a microorganism.

12. The transformant according to claim 10, wherein the host cell is a plant cell.

13. A method for expressing a gene, comprising a step of expressing the desired gene in a host cell under the control of the promoter of claim 1.

14. A method for producing a promoter, comprising a step of ligating a DNA having the following DNA sequence (a) or (b) and a DNA having the nucleotide sequence shown by SEQ ID: No. 1 in a functional form in a host cell, wherein
   (a) is a DNA sequence having the nucleotide sequence represented by at least nucleotide numbers 112–246 within the nucleotide sequence shown by SEQ ID:No.2, and
   (b) is a DNA sequence having the nucleotide sequence represented by at least nucleotide numbers 186–282 within the nucleotide sequence shown by SEQ ID:No.3.

15. A method for producing a promoter, comprising a step of ligating a DNA having the following DNA sequence (a) or (b) and a DNA having the nucleotide sequence shown by SEQ ID:No.1 in a functional form in a host cell, wherein
   (a) is any nucleotide sequence represented by nucleotide numbers 186–282, nucleotide numbers 54–246 or nucleotide numbers 1–246 within the nucleotide sequence shown by SEQ ID:No.2, and
   (b) is any nucleotide sequence represented by nucleotide numbers 186–282, nucleotide numbers 127–282 or nucleotide numbers 1–282 within the nucleotide sequence shown by SEQ ID:No.3.

16. A transformant wherein the chimeric gene of claim 6 is introduced into a host cell.

17. The transformant according to claim 16, wherein the host cell is a microorganism.

18. The transformant according to claim 16, wherein the host cell is a plant cell.

19. A transformant wherein the vector of claim 7 is introduced into a host cell.

20. The transformant according to claim 19, wherein the host cell is a microorganism.

21. The transformant according to claim 19, wherein the host cell is a plant cell.

* * * * *